(12) United States Patent
Assia

(10) Patent No.: US 7,942,889 B2
(45) Date of Patent: May 17, 2011

(54) INTRAOCULAR CLIP

(75) Inventor: Ehud Assia, Tel-Aviv (IL)

(73) Assignee: Hanita Lenses, Hanita (IL)

( * ) Notice: Subject to any disclaimer, the term of this patent is extended or adjusted under 35 U.S.C. 154(b) by 581 days.

(21) Appl. No.: 11/957,569

(22) Filed: Dec. 17, 2007

(65) Prior Publication Data
US 2009/0118746 A1    May 7, 2009

Related U.S. Application Data

(63) Continuation of application No. 11/013,431, filed on Dec. 17, 2004, now abandoned.

(51) Int. Cl.
*A61B 17/03* (2006.01)
(52) U.S. Cl. .............. 606/151; 623/6.12; 623/6.38
(58) Field of Classification Search .......... 606/107, 606/151–158, 166, 204.25, 232; 600/236; 623/4.1, 5.11–6.55
See application file for complete search history.

(56) References Cited

U.S. PATENT DOCUMENTS

| 2,938,252 | A | | 5/1960 | Scheemaeker | |
|---|---|---|---|---|---|
| 4,270,230 | A | * | 6/1981 | Poler | 623/6.41 |
| 4,485,498 | A | * | 12/1984 | Gimbel | 623/6.39 |
| 4,494,254 | A | | 1/1985 | Lopez | |
| 4,961,745 | A | | 10/1990 | Graham | |
| 5,655,266 | A | | 8/1997 | Gish | |
| 5,843,184 | A | * | 12/1998 | Cionni | 623/4.1 |
| 6,537,286 | B2 | | 3/2003 | Acampora et al. | |
| 2008/0103513 | A1 | * | 5/2008 | Assia | 606/151 |

* cited by examiner

*Primary Examiner* — Anhtuan T Nguyen
*Assistant Examiner* — Kathleen Sonnett
(74) *Attorney, Agent, or Firm* — Dekel Patent Ltd.; David Klein

(57) ABSTRACT

An intraocular clip including first and second hook members extending generally coplanarly in opposite directions from a spine, the spine being formed with an attachment member attachable to ocular structure.

6 Claims, 3 Drawing Sheets

INTRAOCULAR CLIP

CROSS-REFERENCE TO RELATED APPLICATIONS

This application claims priority under 35 USC §119 and is a continuation of U.S. patent application Ser. No. 11/013,431, filed Dec. 17, 2004 now abandoned.

FIELD OF THE INVENTION

The present invention relates generally to eye implants for human eyes and, more particularly, to an intraocular clip that may be used to affix the capsular bag to adjoining ocular tissue.

BACKGROUND OF THE INVENTION

As is well known in the art of cataract surgery, a continuous curvilinear capsulorhexis is performed on the anterior capsule to remove the natural lens. The anterior capsule has a generally smooth surface contour except at the equator, where the zonules attach. In such a case, the IOL generally remains well centered postoperatively after the continuous curvilinear capsulorhexis. However, in certain cases, the capsular bag may become decentered. For example, dehiscence or rupture of some of the zonules may cause an uneven zonular tension and decentration of the lens. If an artificial lens is situated within a capsular bag with partial zonular support, the IOL optic edge or elements of the haptic may be situated in the visual axis leading to blurred vision, monocular diplopia and optical aberrations. Contraction of the capsular bag by late fibrosis may further aggravate the vision disturbances.

Capsular tension rings have been used in patients with unstable or absent zonules during cataract surgery, with the aim of minimizing IOL decentration. The capsular tension ring may stabilize the capsular bag, may reduce asymmetric zonular forces, and may reduce capsular decentration during capsular contraction.

For example, capsular bag implants for stabilizing the capsular bag are commercially available from such manufacturers as Morcher GmbH of Stuttgart, Germany, and Hanita Lenses of Hanita, Israel. The capsular bag implant (endocapsular tension ring) comprises an open-ended loop of polymethylmethacrylate (PMMA) which is resilient to compression in the radial direction within the capsular bag. The capsular bag implant is adapted to be implanted in the residual capsular bag before or after the cataractous lens is removed, and to engage the inner peripheral surface of the residual capsular bag to prevent shrinkage. The general circular expansion of the capsular bag as provided by the capsular bag implant is purported to improve stabilization of the intraocular environment and lens centration during intraocular surgery in patients with limited zonular dialysis or generalized zonular weakness. The capsular bag implant may be sutured to the scleral wall of the eye by passing a loop around the endocapsular tension ring and then passing the suture through the annular anterior capsulorhexis flap or the peripheral edge of the capsular bag. However, passing a suture through the residual capsular bag jeopardizes the residual capsular bag's integrity and therefore jeopardizes long-term IOL centration and stabilization.

U.S. Pat. No. 5,843,184 to Cionni describes another endocapsular tension ring, purported to provide long-term stabilization and centralization of the capsular bag during and after intraocular surgery in patients having missing or damaged zonules. The endocapsular tension ring includes an open-ended loop formed of biocompatible material that is constructed to be resilient to compression in the radial direction within the capsular bag to prevent shrinkage of the capsular bag during and after intraocular surgery. The improved endocapsular tension ring includes a fixation element joined to the open-ended loop that is adapted to be attached to the scleral wall of the eye and thereby stabilize and centralize the capsular bag within the posterior chamber of the eye without passing sutures through the capsular bag.

U.S. Pat. No. 6,183,480 to Mackool describes a stabilizer or fixation device. The stabilizer includes a shaft, a stabilizing bend extending from the shaft, and a shank terminating at a termination end. The bend is between the shank and the shaft and is configured to provide a hook-like configuration to the stabilizer. A distance between a trough of the stabilizing bend and the termination end is between 1.6 mm and 5.0 mm, preferably about 2.5 mm and between 2.0 mm and 3.0 mm. The Mackool device is designed for temporary fixation and is not a device which may be permanently left in the eye.

SUMMARY OF THE INVENTION

The present invention seeks to provide novel intraocular clip that may be used to affix the capsular bag to adjoining ocular tissue, as is described more in detail hereinbelow.

There is thus provided in accordance with an embodiment of the invention apparatus including an intraocular clip including first and second hook members extending generally coplanarly in opposite directions from a spine, the spine being formed with an attachment member attachable to ocular structure.

In accordance with an embodiment of the invention a curved crook may be formed between each of the hook members and one end of the spine and the attachment member may be positioned adjacent an opposite end of the spine. The hook members may include arms spaced from the spine on opposite sides of the spine. The arms may be generally parallel to the spine, or alternatively, may be tilted at a non-zero angle with respect to the spine.

Further in accordance with an embodiment of the invention the attachment member may include an enlarged head with at least one hole formed therethrough. The attachment member may include a pair of holes symmetric about a longitudinal axis of the spine.

The enlarged head may or may not protrude outwards beyond an outer edge of the hook members.

BRIEF DESCRIPTION OF THE DRAWINGS

The present invention will be understood and appreciated more fully from the following detailed description, taken in conjunction with the drawings in which.

DETAILED DESCRIPTION OF EMBODIMENTS

Figure 1:
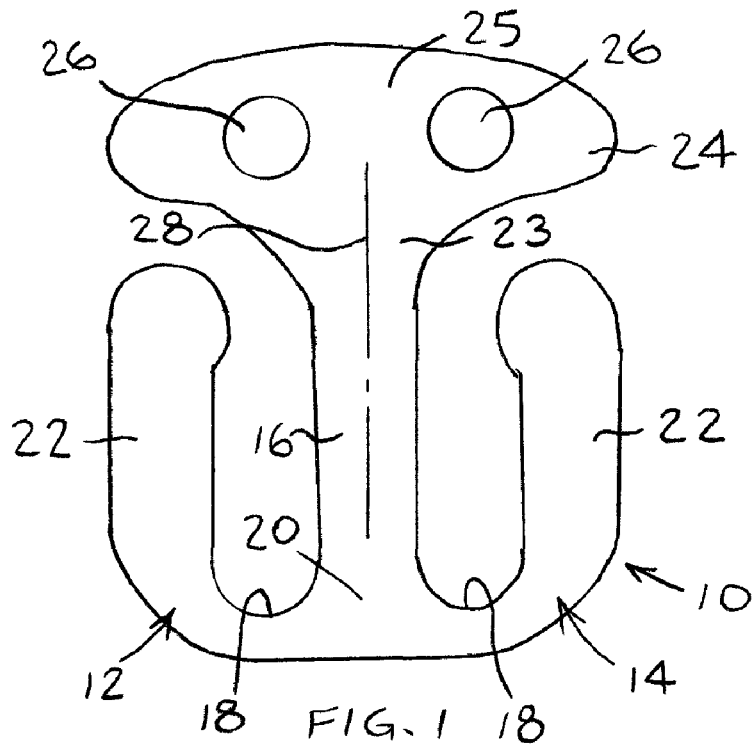
FIG. 1 is a simplified pictorial illustration of an intraocular clip, constructed and operative in accordance with an embodiment of the present invention.

Reference is now made to FIG. 1, which illustrates an intraocular clip 10, constructed and operative in accordance with an embodiment of the present invention.

The intraocular clip 10 may include first and second hook members 12 and 14 extending in opposite directions from a spine 16. The first and second hook members 12 may be generally coplanar with spine 16. In the illustrated non-limiting embodiment, spine 16 is common to, that is, shared by both hook members 12 and 14. A curved crook 18 may be formed between each of hook members 12 and 14 and one end 20 of spine 16. Each of the hook members 12 and 14 may include arms 22 spaced from spine 16 on opposite sides of spine 16. In the illustrated non-limiting embodiment, the arms 22 are generally parallel to spine 16.

The intraocular clip 10 may be constructed of a biologically compatible material, such as but not limited to, polymethylmethacrylate (PMMA), silicone, silicone rubber, collagen, hydrogel, hyaluronic acid (including the sodium, potassium and other salts thereof), polysulfones, thermolabile materials and other relatively hard or relatively soft and flexible biologically inert optical materials. The intraocular clip 10 may be transparent or may be colored to be translucent to aid the surgeon during installation thereof.

The intraocular clip 10 may have any length, width and thickness suitable for intraocular insertion.

The spine 16 may be formed with an attachment member 24 attachable to ocular structure. The attachment member may be positioned adjacent an opposite end 23 of spine 16. The attachment member 24 may include an enlarged head 25 with at least one hole 26 formed therethrough. In the illustrated non-limiting embodiment, the attachment member 24 includes a pair of holes 26 symmetric about a longitudinal axis 28 of spine 16. In the embodiment of FIG. 1, the enlarged head 25 does not protrude outwards beyond an outer edge of hook members 12 and 14.

Figure 2:
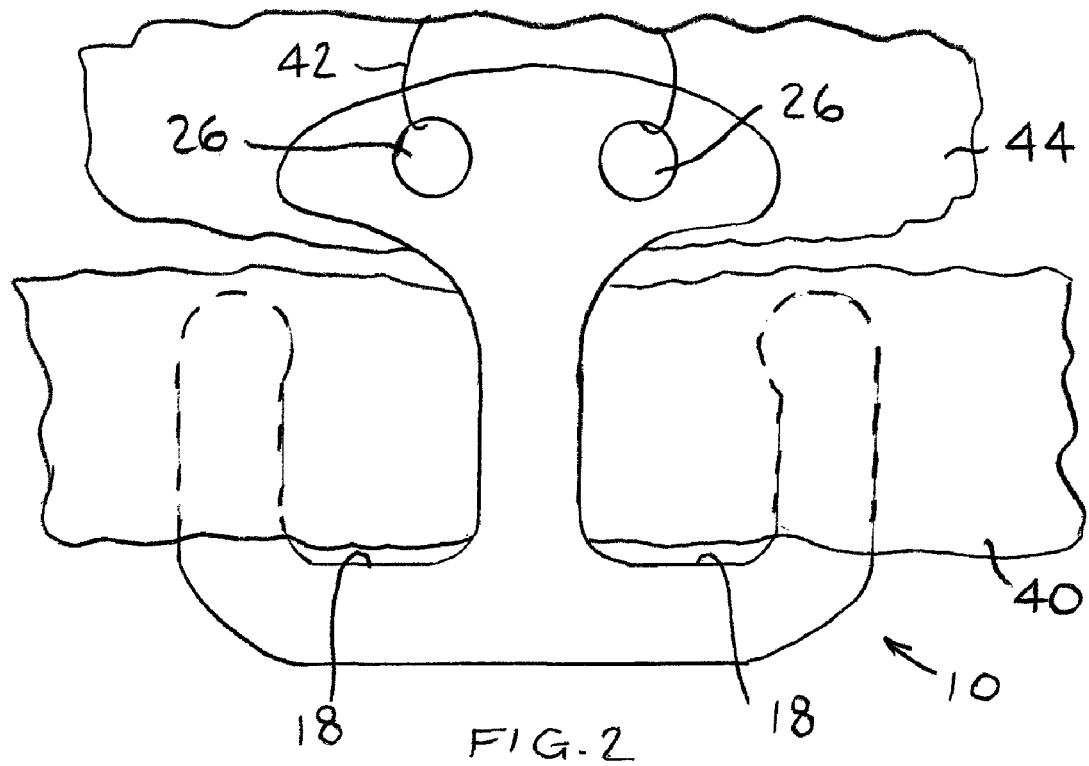
FIG. 2 is a simplified pictorial illustration of an intraocular clip, constructed and operative in accordance with another embodiment of the present invention.
Figure 3:
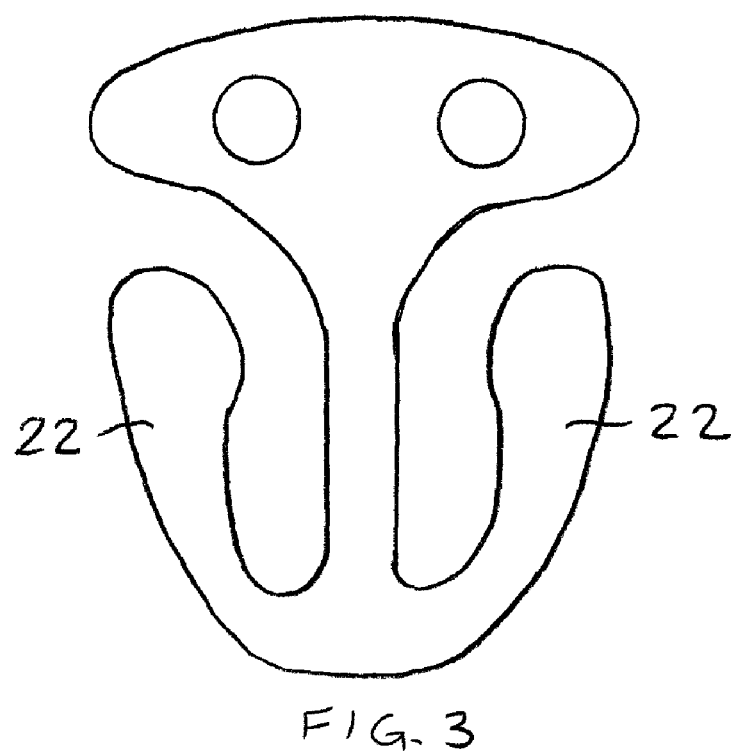
FIG. 3 is a simplified pictorial illustration of an intraocular clip, constructed and operative in accordance with yet another embodiment of the present invention.
Figure 4:
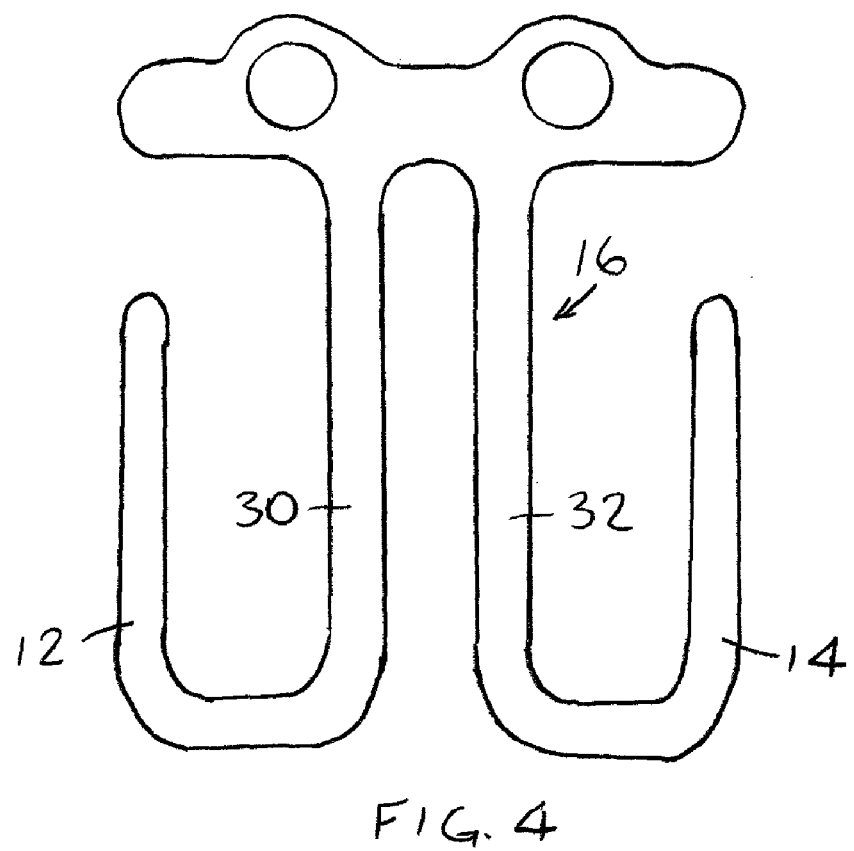
FIG. 4 is a simplified pictorial illustration of an intraocular clip, constructed and operative in accordance with still another embodiment of the present invention.

Reference is now made to FIGS. 2-4, which illustrate non-limiting variations of the intraocular clip 10, constructed and operative in accordance with other embodiments of the present invention.

In the embodiment of FIG. 2, the curved crooks 18 are elongated. In the embodiment of FIG. 3, the arms 22 are tilted at a non-zero angle with respect to spine 16. In addition, the enlarged head 25 protrudes outwards beyond an outer edge of at least one (e.g., both) of the hook members 12 and 14.

Figure 5:
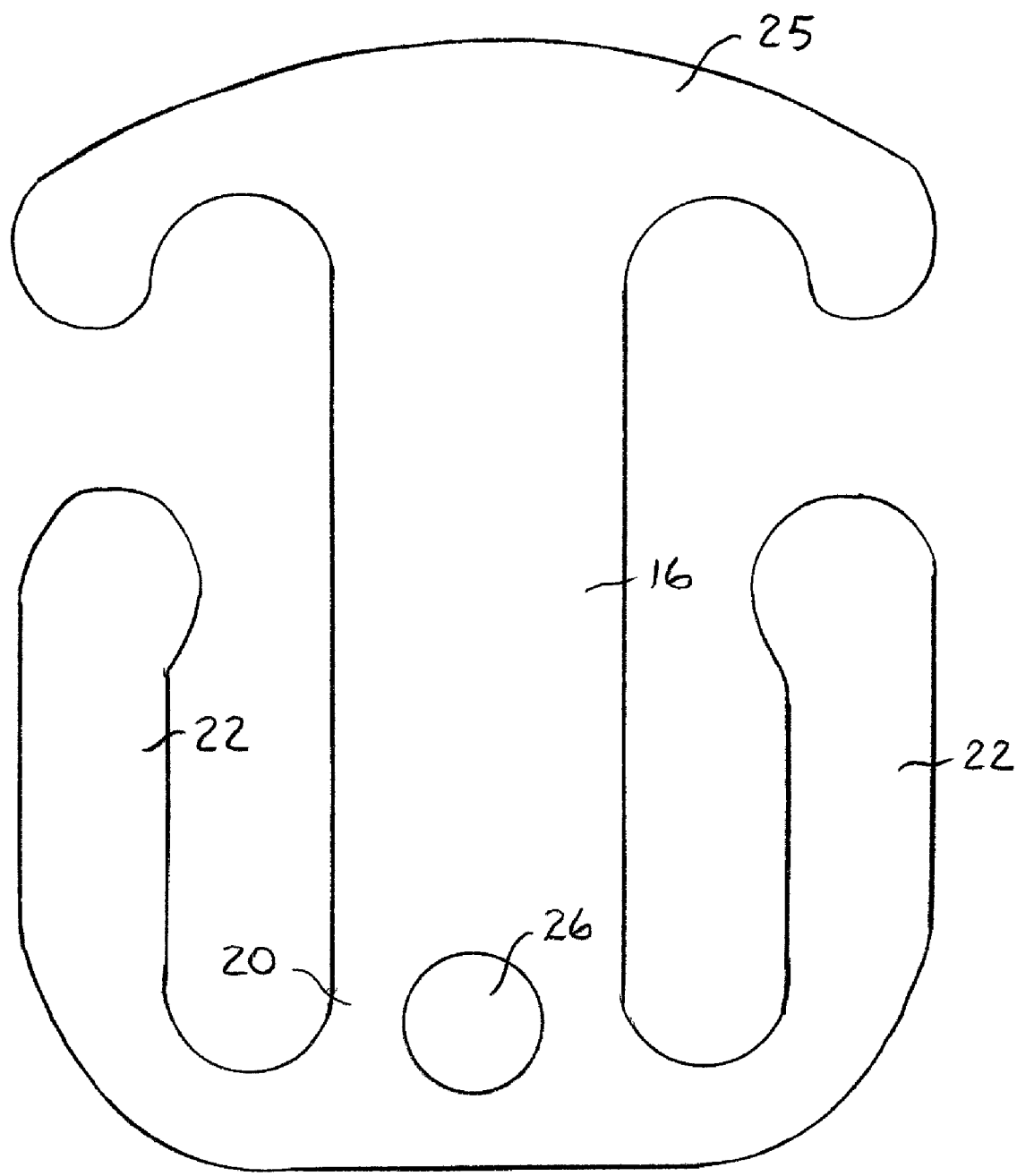
FIG. 5 is a simplified pictorial illustration of an intraocular clip, constructed and operative in accordance with another embodiment of the present invention.

In the embodiment of FIG. 4, the spine 16 comprises two legs 30 and 32, wherein the first hook member 12 extends from leg 30 and the second hook member 14 extends from the other leg 32. In the embodiment of FIG. 5, one or more holes 26 may be formed near end 20 of spine 16, through which sutures may be passed. The enlarged head 25 may be formed with a wavy or curved contour, which may be used for wrapping sutures therearound. It is emphasized that these are just some exemplary embodiments, and the invention is not limited to these examples.

During cataract surgery, the clip may be inserted through a standard incision used for inserting IOLs (e.g., 3 mm). As another example, the intraocular clip 10 may be inserted through the opening made by the capsulorhexis, such as the annular anterior capsulorhexis flap or the peripheral edge of the capsular bag. The intraocular clip 10 may clip the capsular bag in paper-clip fashion. For example, as seen in FIG. 2, the intraocular clip 10 may be hooked onto a capsular bag 40 such that the hook members 12 and 14 are inside the capsular bag 40, while the spine 16 is outside the capsular bag 40. The intraocular clip 10 may be affixed with a suture 42 that passes through the holes 26 and which is tied to ocular structure 44, such as but not limited to, the sulcus, scleral wall or other tissue near the iris or cornea. Additionally or alternatively, suture 42 may be wrapped around the spine 16 or any other portion of clip 10. Safety sutures may be temporarily wrapped around any portion of clip 10 or passed through other holes formed in clip 10. The suture may also be used as a preventative measure to prevent the clip 10 from dropping.

In some situations, one clip may be used. In other situations, two or more clips may be used to symmetrically attach the capsular bag to the ocular structure. The clips may pull vectorially on the capsular bag and may help center it. The clips may be used before or after insertion of the IOL into the capsular bag. The procedure is reversible, and the clips may be removed. The position of the bag may be adjusted by tightening or loosening the sutures when suturing the clip.

The clips may also be used as a corrective measure in cases where a lens was implanted in the past and became decentered. The clip may be used with or without an endocapsular ring. The clip may be used before or after installing an endocapsular ring, before or after installing an IOL, or before or after removal of the crystalline lens. The clip may be used for temporarily clipping and widening the iris, for example.

The scope of the present invention includes both combinations and subcombinations of the features described hereinabove as well as modifications and variations thereof which would occur to a person of skill in the art upon reading the foregoing description and which are not in the prior art.

What is claimed is:

1. A method comprising:
   providing an intraocular clip comprising first and second generally planar hook members extending generally coplanarly in opposite directions from a generally planar spine, said spine being formed with an attachment member attachable to ocular structure;
   inserting said intraocular clip into an eye; and
   clipping said intraocular clip onto a capsular bag in paper-clip fashion by hooking said intraocular clip onto the capsular bag such that said hook members and said spine are on different sides of the capsular bag and such that said spine is straight and extends along a straight line between said hook members when said intraocular clip is clipped onto the capsular bag, and wherein intraocular clip is hooked onto the capsular bag such that the hook members are inside the capsular bag, while the spine is outside the capsular bag.

2. The method according to claim 1, further comprising affixing said intraocular clip with a suture that passes through holes formed in said intraocular clip and tying said suture to ocular structure comprising at least one of a sulcus, a scleral wall and tissue near an iris or a cornea of the eye.

3. The method according to claim 2, further comprising wrapping said suture around a portion of said intraocular clip.

4. The method according to claim 1, further comprising attaching two or more said intraocular clips to the capsular bag to symmetrically attach the capsular bag to ocular structure.

5. The method according to claim 1, wherein a curved crook is formed between each of said hook members and one end of said spine, and clipping said intraocular clip onto the capsular bag further comprises positioning said curved crooks adjacent an edge of said capsular bag.

6. The method according to claim 1, wherein said hook members are generally parallel to said spine when said intraocular clip is clipped onto the capsular bag.

* * * * *